United States Patent
Lorenz et al.

(12)

(10) Patent No.: US 6,302,920 B1
(45) Date of Patent: Oct. 16, 2001

(54) COMPOSITION FOR DYEING AND BLEACHING OF HUMAN HAIR AND PROCESS FOR ITS PREPARATION

(75) Inventors: Heribert Lorenz, Gross-Bieberau; Peter Hirschfeld, Freiburg i. Breisgau; Walter Eberling, Riedstadt, all of (DE)

(73) Assignee: Goldwell AG (DE)

( * ) Notice: Subject to any disclaimer, the term of this patent is extended or adjusted under 35 U.S.C. 154(b) by 0 days.

(21) Appl. No.: 09/430,889

(22) Filed: Nov. 1, 1999

Related U.S. Application Data

(62) Division of application No. 08/456,422, filed on May 31, 1995, now abandoned, which is a continuation of application No. 08/257,882, filed on Jun. 10, 1994, now abandoned.

(30) Foreign Application Priority Data

Jun. 25, 1993 (DE) .................................. 43 21 130
Oct. 7, 1993 (DE) .................................. 43 34 183

(51) Int. Cl.[7] .................................. A61K 7/135
(52) U.S. Cl. .................. 8/111; 132/208; 424/62
(58) Field of Search .................. 8/405, 431, 524; 8/580, 101, 107, 108.1, 111, 102, 112; 424/62, 70.1; 252/186.25, 186.26, 186.27; 132/208

(56) References Cited

U.S. PATENT DOCUMENTS

| | | | |
|---|---|---|---|
| 3,726,967 | 4/1973 | Vorsatz et al. | 424/62 |
| 3,960,476 | 6/1976 | Chilardi et al. | 8/524 |
| 3,981,678 | 9/1976 | Ghilardi et al. | 8/524 |
| 3,983,254 | 9/1976 | Alterman et al. | 252/96 |
| 4,003,841 | 1/1977 | Hachmann et al. | 252/95 |
| 4,009,113 | 2/1977 | Green et al. | 252/95 |
| 4,124,734 | 11/1978 | Alterman et al. | 252/187 C |
| 4,215,990 | 8/1980 | Barrett, Jr. et al. | 8/107 |
| 4,247,537 | 1/1981 | Lunn et al. | 424/62 |
| 4,421,669 | 12/1983 | Brichard | 252/186.26 |
| 4,602,913 | 7/1986 | Grollier et al. | 8/405 |
| 4,604,100 | 8/1986 | Schneider et al. | 8/524 |
| 4,624,678 | 11/1986 | Schneider | 8/524 |
| 4,750,908 | 6/1988 | Rosenbaum et al. | 8/405 |
| 4,919,841 | 4/1990 | Kamel et al. | 252/186.25 |
| 5,063,044 | 11/1991 | Kohl et al. | 424/70 |
| 5,206,385 | 4/1993 | Login et al. | 548/543 |
| 5,279,313 | 1/1994 | Clausen et al. | 132/208 |
| 5,447,654 | * 9/1995 | Millequant et al. | 252/186.25 |
| 5,458,801 | 10/1995 | Oyashiki et al. | 252/186.38 |
| 5,575,989 | * 11/1996 | Caskey | 424/62 |
| 5,989,530 | * 11/1999 | Lorenz et al. | 424/62 |

FOREIGN PATENT DOCUMENTS

| | | |
|---|---|---|
| 1067411 | 12/1979 | (CA) . |
| 2023922 | 11/1970 | (DE) . |
| 3434486 | 3/1986 | (DE) . |
| 3530270 | 2/1987 | (DE) . |
| 0560088 | 9/1993 | (EP) . |
| 4026235 | 9/1993 | (DE) . |

* cited by examiner

*Primary Examiner*—Caroline D. Liott
(74) *Attorney, Agent, or Firm*—Norris, McLaughlin & Marcus, PA

(57) ABSTRACT

A flowable pulverulent bleaching or dyeing composition for human hair with improved properties of use, particularly dustlessness and good miscibility with water or aqueous hydrogen peroxide solution, is obtained by addition, preferably by a melting or spraying process, of about 5% to about 30% by wt. of at least one wax compound having a melting point between about 40° C. and about 130° C., preferably a $C_{12}$–$C_{18}$-fatty acid mono- and (or) dialkanolamide, between about 40° C. and about 130° C. to a powder comprising at least one solid compound exerting bleaching activity upon application on human hair or at least one direct hair dye.

23 Claims, No Drawings

COMPOSITION FOR DYEING AND BLEACHING OF HUMAN HAIR AND PROCESS FOR ITS PREPARATION

This application is a divisional application of U.S. Ser. No. 08/456,422, filed May,31, 1995, now abandoned, which is a continuation of U.S. Ser. No. 08/257,882, filed Jun. 10, 1994, now abandoned.

BACKGROUND OF THE INVENTION

This invention comprises a pulverulent composition for dyeing and bleaching human hair having improved properties, and a process for the preparation of said composition.

Conventional compositions for brightening or bleaching of human hair contain at least one solid peroxide, especially a persulfate, and a pulverulent carrier. Before application onto the hair, this powder is mixed with a 6% to 12% solution of hydrogen peroxide. Examples of such compositions are disclosed in the cosmetic literature, e.g. K. Schrader, "Grundlagen und Rezepturen der Kosmetika", 2nd Ed. (1989, Hüthig Buchverlag), pp. 815 to 823.

The properties of these bleaching powders, however, are not yet satisfactory. On the one hand they develop dust when used, on the other hand their dosage cannot be measured exactly enough so as to affect the desired bleaching result.

The same refers to the well-known pulverulent compositions for direct dyeing of human hair on the basis of natural dyestuffs and direct dyes, which are mixed with water before application.

It has now been found that a pulverulent composition for hair bleaching and dyeing, which does not show the disadvantages mentioned, can be obtained if the composition comprises at least one bleaching compound, preferably a solid peroxide compound, or at least one pulverulent direct dye, along with a pulverulent carrier such as silica, for example pyrogenic silica or diatomasceous earth or starch, and about 5% to about 30% by weight of at least one wax or wax-like substance having a flow point between about 40° C. to about 130° C.

The powder thus prepared and agglomerated or coated is not only completely dustless or at least substantially free of uncoated or unagglomerated dust-forming particles, but also easily flowable, it allows precise dosage and, therefore, convenient mixing with water or a hydrogen peroxide solution before its application onto human hair.

These properties can be improved in a preferred embodiment of the invention by the addition of low quantities of a surfactant to the powder, e.g. a long-chain alkyl sulfate or alkyl ether sulfate, a fatty acid alcohol ethoxylate, an alkylphenol ethoxylate, a polyoxyethylene sorbitan monooleate, laurate or stearate or glycerol-mono- or distearate.

Granulated hair bleaching powders are already known from German Patent Application No. 2,023,922; those are made from per salts and water-soluble binding agents, preferably polyvinyl pyrrolidone. These granules, however, cannot solve the problems indicated above, because they are relatively large-sized particles in the range of millimeters rather than microns so that problems of homogeneous mixing with aqueous hydrogen peroxide arise on the one hand; on the other hand the preparation of these products is relatively expensive in comparison to the bleaching and dyeing powders of the invention which are preferably prepared by melting the wax or wax-like substance together with the solid bleaching compound or the mixture comprising the dyeing compound, or by spraying it onto such mixtures.

The same applies to the granules disclosed in German Patent Application No.4,026,235, the products of which practically correspond with those described in German Patent Application No.2,023,922 previously mentioned.

In principle all natural and synthetic waxes having a flow point within an optimal range of 40° C. to 130° C., preferably from 50° C. to 100° C., are suitable provided that they do not affect the dissolving or dispersing properties of the composition in the aqueous hydrogen peroxide solution.

Suitable waxes are especially polyethylene glycol waxes having a molecular weight between about 600 and 12,000, particularly from 1,500 to 10,000, wherein mixtures of polyethylene glycol waxes of higher or lower molecular weight may also be used, provided the flow point of the mixture is within the range of the invention.

An example for such a composition is a combination of about 10% to 30%, preferably about 20% by wt. of a polyethylene glycol having a molecular weight of about 400 to about 800, particularly about 600, and about 70 to 90, preferably about 80 parts by weight of a polyethylene glycol wax having a molecular weight of about 9,000 to 11,000, preferably about 10,000.

Other suitable waxes are for instance esters of $C_{16}$–$C_{32}$-fatty acids and $C_{12}$–$C_{32}$-fatty alcohols such as cetyl palmitate, mineral waxes, beeswax, shellac wax, (hydrogenated) triglycerides, lanolin and the derivatives thereof, spermaceti, paraffin waxes, microparaffins, ozokerite, ceresin wax, candelilla wax, carnauba wax, montan wax, Japan wax, sugar cane wax, cork wax, guarama wax, astrolatum, petrolatum, hydrogenated jojoba waxes, montan ester waxes, mixed waxes containing emulsifiers, such as the commercial products "Tegin®", "Lanette®", "Cutina®", "Dehymuls®", and "Emulgade®", fatty alcohols having a waxy consistency, fatty acid esters of polyvalent alcohols such as glycerol behenate, glycerol palmitate or stearate, polyglycol glycerides, silicone waxes, higher paraffins, etc.

DETAILED DESCRIPTION OF THE INVENTION

According to a particularly preferred embodiment of the invention, $C_{12}$–$C_{18}$-fatty acid alkanolamides are used as wax-like substances. Suitable fatty acid monoalkanolamides are coconut fatty acid monoethanolamide, lauric fatty acid monoethanolamide, myristic fatty acid monoethanolamide, laurinmyristic acid monoethanolamide and oleic acid monoethanolamide, the corresponding diethanolamides as well as isopropanolamides, e.g. lauric acid isopropanolamide.

The term "wax compounds" will be understood to include both waxes and wax-like compounds, i.e. those compounds exhibiting all of the physical properties of a wax.

The proportion of waxes and wax-like substances such as $C_{12}$–$C_{18}$-fatty acid alkanolamides in the compositions according to the invention is between about 5% and about 30% by weight, preferably between about 8% and 25% by wt., most preferred about 10% to about 20% by wt., each calculated to the total composition.

The handling properties of the bleaching or hair dyeing powder according to the invention can be improved by the addition of low quantities of surfactants.

Particularly suitable are anionic and nonionic products such as the well-known $C_{12}$–$C_{18}$-fatty alcohol polyglycol ethers, e.g. those comprising 3 to 15 ethylene oxide units per mole, as well as alkylphenol polyglycol ethers, e.g. nonylphenol polyglycol ether having about 4 to about 10 EO units per mole, glycerol stearates, polyoxyethylene sorbitan fatty acid esters, long-chain alkyl sulfates such as sodium lauryl sulfate and alkyl ether sulfates. Their proportion is preferably about 0.1% to 2.5% by weight, more preferredly 0.15% to 2.5%, most preferredly about 0.25% to 1% by wt., calculated to the total composition of the invention.

Other preferred ingredients of the compositions according to the invention are water-soluble polymers, particularly polyvinyl pyrrolidone, preferably in a quantity of 0.1% to 1% by wt., calculated to the total composition.

The bleaching and (or) dyeing compositions for human hair according to the invention comprise the usual ingredients known in those preparations; to avoid repetition, reference is made to Schrader, l.c., in this context.

Suitable peroxides are preferably alkali persulfates such as potassium and ammonium persulfates, magnesium peroxide, urea peroxide, melamin peroxide, etc., as well as mixtures of these.

Other compositions may also be used which contain no persulfate or only very little thereof; instead they comprise other bleaching or brightening compounds, e.g. ammonium carbonate, ammonium bicarbonate, ammonium phosphates, ammonium citrates, ammonium chloride and (or) ammonium carbamate.

To produce the agglomerized dyeing powder of the invention, the well-known natural dyestuffs may be used, e.g. henna (red, black, or neutral), alkannin or alkanna root powder, logwood powder, madder root powder, rhubarb root powder, etc.

Other suitable dyestuffs are synthetic direct dyes, e.g. the well-known "Arianor" dyes which may be used solely or in admixture with natural dyes.

Corresponding compositions belong to the state of technology and are described in the relevant literature, e.g. in Schrader, l.c., pp. 782 to 806.

According to a preferred embodiment of the invention, the production of the hair bleaching or dyeing composition is performed by spraying the melted wax or wax-like substances, e.g. the $C_{12}$–$C_{18}$-fatty acid alkanolamide, onto the residual powder substances. This takes place at preferably 40° C. to 130° C., more preferredly at 50° C. to 100° C., depending on the melting point of the wax or wax-like substance used.

Another possibility of admixture is to mix the pulverulent substances with the particulate wax or waxy substance by fluidizing and melting the mixture subsequently; after cooling, the agglomerate is ground if necessary.

Suitable procedures and facilities for the performance of this process are known per se, cf. e.g. European Patent Application No.526,394, German Patent Application No.2,030,104, European Patent Application No.244,550, U.S. patent application Ser. No.4,935,246 and French Patent Application No.2,628,014, and reference is expressly made to the disclosures therein.

Another process of preparation is mixing first part of the wax intended for use which has a higher melting point, e.g. polyethylene glycol wax having a molecular weight of 8,000 to 12,000, preferably about 10,000, with the initial pulverulent bleaching composition comprising a carrier substance at about 50° C. to about 100° C., and then spraying the remainder of the liquid wax, e.g. a polyethylene glycol wax having a molecular weight of about 600 and thus a lower melting point, onto the mixture.

The particle size of the bleaching or dyeing compositions according to the invention is normally below 1 mm, preferably below 500 microns, e.g. less than 400 microns, which allows excellent handling, i.e. mixing with water or an aqueous hydrogen peroxide solution, before application onto human hair.

The application of the composition is performed by the usual and known procedures:

By admixture of the pulverulent bleaching composition with a 6% to 12% hydrogen peroxide solution, wherein about 1 part of the powder is mixed with about 1.5 parts of the peroxide solution, preferably a 9% hydrogen peroxide solution, a homogeneous mixture is prepared and applied onto the hair to remain there for processing for about 20 to about 60 minutes.

If the product is a hair dyeing composition according to the invention, it is mixed with water until homogeneous and applied onto the hair for processing.

The following examples illustrate the invention.

EXAMPLE 1

| | |
|---|---|
| Silica (diatomaceous earth) | 3.20% by wt. |
| Silica (pyrogenic silica)) | 5.30 |
| Sodium carboxymethyl cellulose | 3.50 |
| Urea | 2.00 |
| Sodium lauroyl sarcosinate | 0.80 |
| Sodium stearate | 1.20 |
| Sodium carbonate | 1.00 |
| Sodium metasilicate | 6.00 |
| Starch powder | 3.50 |
| Potassium persulfate | 54.50 |
| Magnesium peroxide | 4.00 |
| Coconut monoethanolaimide | 15.00 |

A dustless water-soluble and water-dispersible powder, resp., was obtained which was easily miscible with a known 9% hydrogen peroxide solution in a ratio of 1:1.5. 99% of the particles had a diameter of less than 400 micron.

The production of the powder was performed by heating the above-mentioned mixture to a temperature of 70° C. to 75° C. in a fluidized bed reactor and subsequent cooling.

EXAMPLE 2

The composition of Example 1 was changed inasmuch as 0.15% by wt. of a $C_{12}$–$C_{14}$-fatty alcohol ethoxylate (about 6 ethoxylate units per mole) were added while decreasing the content of coconut monoethanolamide accordingly.

A flowable dustless product was obtained which provided an excellent mixture with a 9% hydrogen peroxide solution.

EXAMPLE 3

The composition according to Example 1 was modified inasmuch, as 0.50% by wt. of sodium lauryl sulfate were added to the composition while decreasing the content of coconut monoethanolamide accordingly.

The free-flowing and (or) pourable bleaching powder obtained by this procedure did not dust and was easily miscible with a 9% hydrogen peroxide solution.

EXAMPLE 4

A composition comprising

| | |
|---|---|
| 32.00 (g) | Ammonium persulfate |
| 25.00 | Potassium persulfate |
| 10.50 | Sodium metasilicate |
| 5.50 | Silica |
| 4.80 | Starch |
| 3.80 | Magnesium peroxide |
| 3.20 | Urea |
| 3.50 | Sodium carboxymethyl cellulose |
| 2.90 | Sodium stearate |
| 1.00 | Sodium lauroyl sarcosinate |
| 2.50 | Diatomaceous earth |
| 1.50 | Complexing agents (Na EDTA) |
| 0.30 | Perfume, | was sprayed with 18.00 g of finely divided coconut monoethanolamide at a temperature of 70° C. to 75° C. in a fluidized bed reactor.

After 15 minutes, the mixture was cooled down to 25° C.; the agglomerate thus obtained was non-dusting and excellently miscible with a 9% hydrogen peroxide solution to obtain a homogeneous hair bleaching composition.

More than 99% of the particles produced according to Example 4 had a diameter between 50 $\mu$m and 500 $\mu$m. The water content was below 1% in each case.

EXAMPLE 5

A mixture comprising

| | | |
|---|---|---|
| 65.0 | (pts. by wt.) | Alkanna root |
| 8.0 | | Henna, black |
| 2.0 | | Sodium alginate |
| 2.0 | | Sodium carboxymethyl cellulose |
| 2.5 | | Sodium carbonate |
| 0.5 | | Sodium lauryl sulfate |
| 0.4 | | Polyvinyl pyrrolidone, | was incorporated into a fluid bed top spray plant and sprayed with 12 parts by weight of coconut fatty acid monoethanolamide at a temperature of about 75° C.

The product thus obtained was completely dustless, had excellent. flowing properties, was non-sticky and miscible with water to obtain a hair dyeing composition for easy application onto the hair, whereupon, after a processing time of 30 to 60 minutes, a graphite gray shade was achieved.

In each case, less than 1% of the particles had a diameter below 50 $\mu$m and above 900 $\mu$m.

EXAMPLE 6

A mixture comprising

| | | |
|---|---|---|
| 67.0 | (parts by wt.) | Henna, red |
| 8.0 | | Henna, black |
| 2.0 | | Basic Blue 99 |
| 1.5 | | Sodium alginate |
| 1.5 | | Sodium carboxymethyl cellulose |
| 0.4 | | Polyvinyl pyrrolidone |
| 1.0 | | Sodium lauryl sulfate and |
| 14.0 | | Coconut fatty acid monoethanolamide, | was prepared, heated in a fluidized bed reactor to a temperature from 70° C. to 75° C., and cooled thereafter.

The agglomerate thus obtained was easily miscible with water in a ratio of 1:4 and provided a dark brown shade on the hair after a processing time of 30 to 60 minutes.

EXAMPLE 7

| | |
|---|---|
| Silica (diatomaceous earth) | 3.20% by wt. |
| Silica (pyrogenic SiO$_2$)) | 5.30 |
| Sodium carboxymethyl cellulose | 3.50 |
| Urea | 2.00 |
| Sodium lauroyl sarcosinate | 0.80 |
| Sodium stearate | 1.20 |
| Sodium carbonate | 1.00 |
| Sodium metasilicate | 6.00 |
| Starch powder | 3.50 |
| Potassium persulfate | 54.50 |
| Magnesium peroxide | 4.00 |
| Polyethylene glycol wax (mol. wt. 10,000) (Flow point: 63° C.) | 15.00 |

A dust-free water-soluble and water-dispersible powder was obtained which was easily miscible with a known 9% hydrogen peroxide solution in a weight proportion of 1:1.5. 99% of the particles had a diameter of less than 400 microns.

The production of the powder was effected by heating the above mixture to a temperature of 70° C. to 75° C. in a fluidized bed reactor, and allowing to cool down thereafter.

EXAMPLE 8

The formulation of Example 7 was changed inasmuch as 0.15% by wt. of a $C_{12}$–$C_{14}$-fatty alcohol ethoxylate (about 6 EO units per mole) was added while reducing the content of polyethylene glycol wax accordingly.

A free-flowing dust-free product was obtained which was excellently miscible with a 9% hydrogen peroxide solution.

EXAMPLE 9

The formulation of Example 7 was changed inasmuch as 0.5% by wt. of a nonylphenol ethoxylate (about 4 EO units per mole) was added while reducing the content of polyethylene glycol wax accordingly.

The bleaching powder thus obtained was free-flowing, non-dusting, and excellently miscible with a 9% solution of hydrogen peroxide.

EXAMPLE 10

A composition was prepared from:

| | |
|---|---|
| 32.00 (g) | Ammonium persulfate |
| 25.00 | Potassium persulfate |
| 10.50 | Sodium metasilicate |
| 5.50 | Silica |
| 4.80 | Starch |
| 3.80 | Magnesium peroxide |
| 3.20 | Urea |
| 3.50 | Sodium carboxymethyl cellulose |
| 2.90 | Sodium stearate |
| 1.00 | Sodium lauroyl sarcosinate |
| 2.50 | Diatomaceous earth |
| 1.50 | Complexing agents (Na EDTA) |
| 0.30 | Perfume, | whereafter it was sprayed with 18.00 g of finely dispersed polyethylene glycol wax (mol.wt. 6,000) at a temperature of 60° C. to 70° C. in a fluid bed reactor.

After 15 minutes, the preparation was cooled down to 25° C.; the agglomerate obtained was non-dusting and excellently miscible with 9% $H_2O_2$-solution to a homogeneous hair bleaching composition.

EXAMPLE 11

A mixture was prepared from:

| | |
|---|---|
| 40.0 g | Magnesium peroxide |
| 330.0 | Ammonium persulfate |
| 250.0 | Potassium persulfate |
| 100.0 | Sodium metasilicate |
| 85.0 | Silica |
| 3.0 | Perfume oil |
| 28.0 | Sodium carboxymethyl cellulose |
| 0.5 | Blue dyestuff |
| 30.0 | Sodium stearate |
| 10.0 | Sodium lauroyl sarcosinate |
| 10.0 | Complexing agents |
| 50.0 | Starch |
| 9.0 | Sodium carbonate, | to which 140 g of polyethylene glycol wax having a molecular weight of about 10,000 were added in a first step, heated to a temperature of about 65° C. to 75° C., whereafter, in the course of about 10 to 15 minutes, 15 g of polyethylene glycol wax having a molecular weight of about 600 were sprayed onto the mixture. After cooling down, a bleaching powder agglomerate was obtained which was non-dusting and easily miscible with 9% hydrogen peroxide solution.

More than 99% of the particles produced according to the Examples 10 and 11 had a diameter between 50 μm and 900 μm. The water content in each case was below 2.5%.

What is claimed is:

1. A process for bleaching of human hair, consisting of the steps of:
   a) preparing a pulverulent composition comprising
      at least one solid active hair bleaching compound chosen from the group consisting of peroxides, ammonium carbonate, ammonium bicarbonate, ammonium citrate, ammonium chloride and ammonium carbamate; and
      a pulverulent carrier chosen from the group consisting of silica and starch,
   b) coating or agglomerating the composition by spraying with at least one melted wax compound, said wax compound having a flow point between about 40 degrees C. and about 130 degrees C., said wax compound being present at about 5–30% by weight of the total composition, said composition having a particle size below 1 mm,
      such that said composition is substantially free of uncoated or unagglomerated particles, to form a substantially dust-free composition,
   c) cooling the composition
   d) mixing said substantially dust-free composition with a hydrogen peroxide solution at 6–12 wt % to form a mixture,
   e) applying said mixture to the hair.

2. The process according to claim 1, wherein said wax compound is present at about 10% to about 25% by weight.

3. The process according to claim 1, wherein said wax compound comprises polyethylene glycol wax having a molecular weight between about 600 and 12,000.

4. The process according to claim 1, wherein the wax compound comprises a wax mixture of about 70 to 90 parts by weight of a polyethylene glycol having a molecular weight of 9,000 to 11,000, and about 10 to 30 parts by weight of a polyethylene glycol having a molecular weight of about 400 to 800.

5. The process according to claim 1, wherein the wax compound comprises at least one of $C_{12}$–$C_{18}$-fatty acid monoalkanolamide and $C_{12}$–$C_{18}$-fatty acid dialkanolamide.

6. The process according to claim 5, wherein the wax compound comprises coconut fatty acid monoalkanolamide.

7. The process according to claim 1, wherein the composition further comprises about 0.1% to about 5% by wt. of a surfactant.

8. The process according to claim 7, wherein the composition comprises about 0.1% to 2.5% by wt. of a nonionic surfactant.

9. The process according to claim 8, wherein the nonionic surfactant comprises one of a fatty alcohol polyglycol ether, an alkylphenol polyglycol ether, glycerol monostearate and glycerol distearate.

10. The process according to claim 7, wherein the composition comprises about 0.1% to 2.5% by wt. of an anionic surfactant.

11. The process according to claim 10, wherein the anionic surfactant comprises at least one of $C_{12}$–$C_{18}$-alkyl sulfate and $C_{12}$–$C_{18}$-ether sulfate.

12. Process for the preparation of a pulverulent composition for bleaching or dyeing of human hair, consisting of the steps of forming the pulverulent composition comprising at least one active bleaching compound and a pulverulent carrier chosen from the group consisting of silica and starch, and then mixing the composition with a wax compound having a flow point between about 40° C. and about 130° C., and thereafter melting at a temperature exceeding the flow-point of the wax compound, whereafter the mixture is cooled to form an agglomerate, optionally grinding the agglomerate, and thereafter mixing said agglomerate with a hydrogen peroxide solution at 6–12 wt % to form a mixture, and applying said mixture to the hair.

13. The process according to claim 12, wherein after the mixture is cooled, the agglomerate is ground before mixing with hydrogen peroxide.

14. The process according to claim 12, wherein said wax compound is present at about 10% to about 25% by weight.

15. The process according to claim 12, wherein said wax compound comprises polyethylene glycol wax having a molecular weight between about 600 and 12,000.

16. The process according to claim 12, wherein the wax compound comprises a wax mixture of about 70 to 90 parts by weight of a polyethylene glycol having a molecular weight of 9,000 to 11,000, and about 10 to 30 parts by weight of a polyethylene glycol having a molecular weight of about 400 to 800.

17. The process according to claim 12, wherein the wax compound comprises at least one of $C_{12}$–$C_{18}$-fatty acid monoalkanolamide and $C_{12}$–$C_{18}$-fatty acid dialkanolamide.

18. The process according to claim 17, wherein the wax compound comprises coconut fatty acid monoalkanolamide.

19. The process according to claim 12, wherein the composition further comprises about 0.1% to about 5% by wt. of a surfactant.

20. The process according to claim 19, wherein the composition comprises about 0.1% to 2.5% by wt. of a nonionic surfactant.

21. The process according to claim 20, wherein the nonionic surfactant comprises one of a fatty alcohol polyglycol ether, an alkylphenol polyglycol ether, glycerol monostearate and glycerol distearate.

22. The process according to claim 19, wherein the composition comprises about 0.1% to 2.5% by wt. of an anionic surfactant.

23. The process according to claim 22, wherein the anionic surfactant comprises at least one of $C_{12}$–$C_{18}$-alkyl sulfate and $C_{12}$–$C_{18}$-ether sulfate.

* * * * *